US009177103B2

(12) United States Patent
Mallya et al.

(10) Patent No.: US 9,177,103 B2
(45) Date of Patent: Nov. 3, 2015

(54) DATA PROCESSING OF GROUP IMAGING STUDIES

(75) Inventors: Yogish Mallya, Bangalore (IN); Shivakumar Kunigal Ramaswamy, Bangalore (IN); Narayanan Ayyakad Krishnan, Bank (IN); Lyubomir Georgiev Zagorchev, Lebanon, NH (US)

(73) Assignee: Koninklijke Philips N.V., Eindhoven (NL)

( * ) Notice: Subject to any disclaimer, the term of this patent is extended or adjusted under 35 U.S.C. 154(b) by 71 days.

(21) Appl. No.: 13/575,772

(22) PCT Filed: Jan. 28, 2011

(86) PCT No.: PCT/IB2011/050378
§ 371 (c)(1),
(2), (4) Date: Jul. 27, 2012

(87) PCT Pub. No.: WO2011/095918
PCT Pub. Date: Aug. 11, 2011

(65) Prior Publication Data
US 2012/0308097 A1     Dec. 6, 2012

Related U.S. Application Data

(60) Provisional application No. 61/300,481, filed on Feb. 2, 2010.

(51) Int. Cl.
*G06F 19/00*     (2011.01)
(52) U.S. Cl.
CPC ............ *G06F 19/321* (2013.01); *G06F 19/363* (2013.01)

(58) Field of Classification Search
USPC .................................................. 382/128–134
See application file for complete search history.

(56) References Cited

U.S. PATENT DOCUMENTS 5,859,891 A * 1/1999 Hibbard ........................... 378/62
6,424,732 B1 * 7/2002 Shiffman et al. ............. 382/131
(Continued)

FOREIGN PATENT DOCUMENTS

EP     1662415 A1     5/2006
JP     214387 H     7/1988
(Continued)

OTHER PUBLICATIONS

Batlle et al, "A Review on Strategies for Recognizing Natural Objects in Colour Images of Outdoor Scenes", Image and Vision Computing, vol. 18, 2000, pp. 515-530.
(Continued)

*Primary Examiner* — Alex Liew (57) ABSTRACT

A system for processing multi-subject volumes comprises a volume input (1) for receiving an input volume image dataset (13) comprising a plurality of subjects scanned simultaneously. A metadata input (2) receives metadata (15) relating to individual ones of the subjects. A subject finder (3) identifies a plurality of portions of the input volume image dataset (13), each portion comprising one of the subjects. A volume image dataset generator (4) generates a plurality of separate volume image datasets (16), each separate volume image dataset (7) comprising one of the portions of the input volume image dataset. A metadata handler (5) associates the metadata (15) relating to a subject with the separate volume image dataset (7) comprising the portion comprising the subject.

19 Claims, 5 Drawing Sheets

(56) References Cited

U.S. PATENT DOCUMENTS

| | | |
|---|---|---|
| 7,043,094 B2 | 5/2006 | Thomas et al. |
| 7,043,236 B2 | 5/2006 | Lee |
| 7,177,453 B2 | 2/2007 | Suryanarayanan et al. |
| 7,953,262 B2 | 5/2011 | Suryanarayanan et al. |
| 2004/0022424 A1 | 2/2004 | Seissler et al. |
| 2005/0207658 A1* | 9/2005 | Schofield ............... 382/232 |
| 2006/0115135 A1* | 6/2006 | Dehmeshki et al. ....... 382/128 |
| 2007/0280556 A1 | 12/2007 | Mullick et al. |
| 2008/0219511 A1* | 9/2008 | Nakajima et al. ........ 382/110 |
| 2008/0298665 A1* | 12/2008 | Kariathungal et al. .... 382/132 |
| 2009/0087049 A1* | 4/2009 | Takahashi .............. 382/128 |
| 2009/0148071 A1 | 6/2009 | Ohwa et al. |
| 2009/0226088 A1 | 9/2009 | Okazawa |
| 2009/0279793 A1 | 11/2009 | Misawa |
| 2009/0285495 A1 | 11/2009 | Wagner |
| 2009/0310836 A1* | 12/2009 | Krishnan et al. ......... 382/128 |
| 2009/0310862 A1 | 12/2009 | Tu et al. |
| 2013/0034203 A1* | 2/2013 | Wang et al. ............ 378/41 |

FOREIGN PATENT DOCUMENTS

| | | |
|---|---|---|
| JP | 10177642 A | 6/1998 |
| WO | 2009040690 A2 | 4/2009 |
| WO | 2009141768 A1 | 11/2009 |

OTHER PUBLICATIONS

Kohlmann, P. et al. "Contextual Picking of Volumetric Structures", pp. 185-192, 2009 IEEE Pacific Visualization Symposium, 2009.

Latecki, L.J. "Image Segmentation", PPT presentation CIS 601 Fall 2004. http://www.powershow.com/view1/cba51-ZDc1Z/Image_Segmentation_powerpoint_ppt_presentation.

Rodriguez, E. et al. "DRM and Access Control architectures interoperability", 50th International Symposium ELMAR-2008, Sep. 10-12, 2008, Zadar, Croatia.

* cited by examiner

DATA PROCESSING OF GROUP IMAGING STUDIES

FIELD OF THE INVENTION

The invention relates to processing multi-subject volumes.

BACKGROUND OF THE INVENTION

Preclinical research is characterized by hypothesis driven programs to either discover or explore new insights into biological processes. A goal of these programs is systematic discovery and development of biomarkers, drugs, and therapies that will ultimately be translated from animal models to humans should they prove promising during preclinical studies. Small animal models of human diseases, particularly genetically engineered mice, are widely used in preclinical studies. Studies on distributed population groups (example group of animals which received a drug vs. control group of animals) are done to substantiate the hypothesis.

In vivo imaging permits both the temporal and the spatial bio-distribution of a molecular probe and related biological processes to be determined in a more meaningful manner throughout an intact living subject. It is possible to image multiple subjects simultaneously in a scanner in order to achieve higher throughput. Processing, evaluation and visualization of resulting image data may be performed using a pre-clinical workstation, such as the IMALYTICS Workspace from Philips Healthcare.

SUMMARY OF THE INVENTION

It would be advantageous to have an improved processing of multi-subject volumes. To better address this concern, a first aspect of the invention provides a system comprising
  a volume input for receiving an input volume image dataset comprising a plurality of subjects scanned simultaneously;
  a metadata input for receiving metadata relating to individual ones of the subjects;
  a subject finder for identifying a plurality of portions of the input volume image dataset, each portion comprising one of the subjects;
  a volume image dataset generator for generating a plurality of separate volume image datasets, each separate volume image dataset comprising one of the portions of the input volume image dataset; and
  a metadata handler for associating the metadata relating to a subject with the separate volume image dataset comprising the portion comprising the subject.

When multiple subjects are scanned simultaneously in an image scanner, a volume image dataset may result in which all scanned subjects are visible. However, organizing or evaluating these data is difficult, because the dataset comprises a plurality of subjects which may have different metadata applicable to them. By generating separate volume image datasets having the appropriate metadata associated therewith, it becomes possible to search for images of individual subjects by means of the associated metadata. Also visualization of a single subject is improved, because the view of one subject is not disturbed by the other subjects.

The volume image dataset generator may comprise a file generator for generating a file comprising the separate volume image dataset. Moreover, the metadata handler may be operatively connected to the volume image dataset generator for including the metadata in the file. The file is a convenient format to store and/or transmit the separate volume image dataset.

The separate volume image dataset may be in a DICOM format. The metadata may be represented as DICOM attributes. This allows the DICOM format to be used for the separate volume image datasets. Consequently, DICOM tools may be used for the processing and/or data-mining of the separate volume image datasets. For example, the file may be a DICOM file in which the metadata may be stored as DICOM attributes.

The volume input may be arranged for receiving the input volume image dataset in a DICOM format. This allows the system to receive data from DICOM imaging equipment, such as a medical image scanner and/or a DICOM-based medical image repository.

The plurality of subjects may belong to different study groups, and the metadata may be indicative of the study group a subject belongs to. This way, searching for scans of different subject groups is made easier. It is difficult to search scans of subjects belonging to a particular study group if they are incorporated in an image volume scan comprising subjects from different study groups.

The metadata input may comprise a user interface element for enabling a user to enter information fields relating to each of the subjects. This allows the user to determine the metadata to be associated with each of the subjects.

The metadata input may be arranged for receiving metadata indicative of an identifier of an individual one of the subjects. An identifier is a useful form of metadata as it identifies the subject. Other metadata may also be included.

The metadata handler may be arranged for associating an identifier of the input volume image dataset with the separate volume image dataset. This allows tracing back the input volume image dataset from the separate volume image dataset.

The system may further comprise a query input for receiving a query, and a search engine for searching one or more separate volume image datasets of which the metadata matches the query. This allows finding the separate volume image datasets based on the metadata.

The system set forth may be included in a pre-clinical workstation.

An image acquisition apparatus may further comprise an image scanner for acquiring an input volume image dataset comprising a plurality of subjects scanned simultaneously. This allows acquiring the input volume image dataset and generating the separate volume image datasets with the same apparatus.

Another aspect of the invention provides a method of processing multi-subject volumes, comprising
  receiving an input volume image dataset comprising a plurality of subjects scanned simultaneously;
  receiving metadata relating to individual ones of the subjects;
  identifying a plurality of portions of the input volume image dataset, each portion comprising one of the subjects;
  generating a plurality of separate volume image datasets, each separate volume image dataset comprising one of the portions of the input volume image dataset; and
  associating the metadata relating to a subject with the separate volume image dataset comprising the portion comprising the subject.

Another aspect of the invention provides a computer program product comprising instructions for causing a processor system to perform the method set forth.

It will be appreciated by those skilled in the art that two or more of the above-mentioned features, embodiments, implementations, and/or aspects of the invention may be combined in any way deemed useful.

Modifications and variations of the image acquisition apparatus, the workstation, the system, the method, and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

In the following, aspects of the invention will be described in more detail. However, it will be understood that the description only serves to illustrate possible embodiments of the invention and their advantages. Modifications of these embodiments are within reach of the skilled person.

Figure 1:
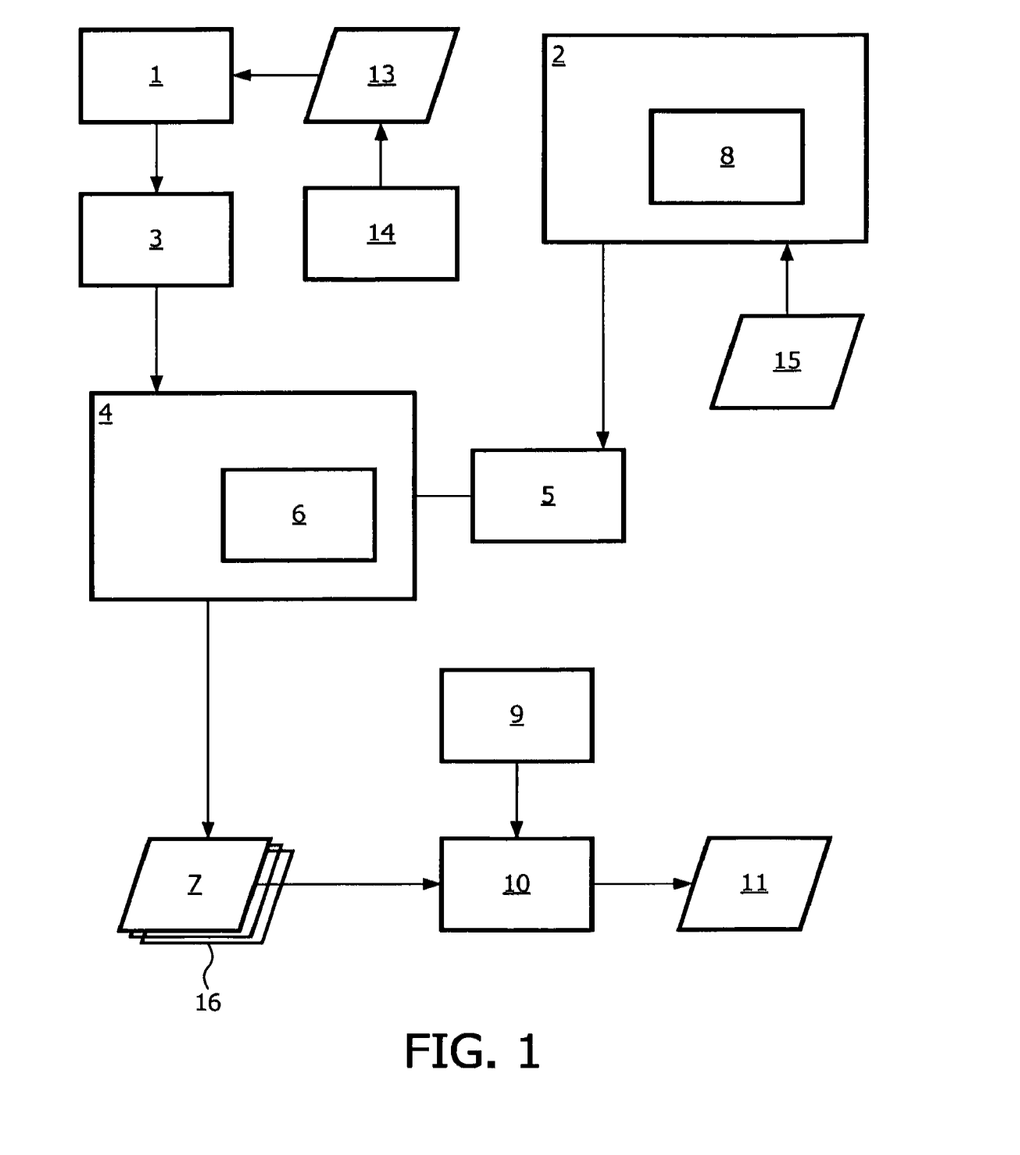
FIG. 1 is a diagram of a system for processing multi-subject volumes.

FIG. 1 illustrates a system for processing multi-subject volumes. The system may be implemented in different ways, for example by means of a suitably programmed computer. Other implementations are also possible, including a dedicated electronic circuit.

The system may comprise a volume input 1 for receiving an input volume image dataset 13, which may comprise a plurality of subjects scanned simultaneously. For example, the volume input 1 comprises a disk interface or a network connection with an image repository. Volume input 1 may also comprise a direct connection with an image scanner 14. The system may further comprise a metadata input 2 for receiving metadata 15 relating to individual ones of the subjects.

A subject finder 3 may be arranged for analyzing the input volume image dataset 13. The subject finder 3 may attempt to identify a plurality of portions of the input volume image dataset 13, each portion comprising one of the subjects. If the attempt is not successful, it is possible to stop processing the input volume image dataset 13, because it may comprise only one subject. Alternatively, the system may comprise a user interface element to enable a user to indicate the portions. When the portions have been identified, they may be forwarded to a volume image dataset generator 4, for generating a plurality of separate volume image datasets 16. Each separate volume image dataset 7 comprises one of the portions of the input volume image dataset. This way, each separate volume image dataset comprises one of the subjects.

A metadata handler 5 may be arranged for associating the appropriate metadata 15 with the separate volume image datasets 16. In particular, the metadata 15 received for a particular subject is associated with the corresponding separate volume image dataset 7 comprising the portion comprising that particular subject. Herein, "portion" refers to the portion of the input volume image dataset.

The volume image dataset generator 4 may comprise a file generator 6. The file generator 6 may be arranged for generating a file, for example a file in a file system. File generator 6 may be arranged for invoking appropriate operating system calls for this. In another example, the file may be transmitted as a data stream. The file comprises a separate volume image dataset 7. The metadata handler 5 may be operatively connected to the volume image dataset generator 4, such that the appropriate metadata is included in the file with the separate volume image dataset comprising the corresponding subject. However, it is also possible to store the metadata together with a reference to the corresponding separate volume image dataset 7 in a table or a database. Other ways of associating the metadata with the separate volume image dataset 7 are also possible. The file generated by the file generator 6 may be a DICOM file. However, this is not a limitation. Other file formats to store and/or transmit the separate volume image file are apparent to the person skilled in the art.

In general, the separate volume image dataset 7 may be in a DICOM format, wherein the metadata are represented as DICOM attributes. For example, the separate volume image dataset 7 may be represented as a DICOM stream which may be transmitted over a network, for example.

The volume input 1 may be arranged for receiving the input volume image dataset 13 in a DICOM format. Accordingly, the image scanner 14 may be arranged to generate the input volume image dataset 13 in a DICOM format.

DICOM is shorthand for "Digital Imaging and Communications in Medicine". It is an industry standard which defines the format of different kinds of image data used in medicine.

It is possible that the plurality of subjects comprised in the input volume image dataset belong to different study groups. For example some of the subjects may belong to a first study group, and some others may belong to a second study group. The metadata 15 may be indicative of the study group a subject belongs to. For example, the metadata 15 may comprise an identifier of the appropriate study group for a subject. The metadata handler may be arranged for associating that metadata, i.e. that identifier, with the separate volume image dataset comprising that subject. This association may be done in a way described herein, for example by inclusion in a file or a DICOM file, or in any other way.

The system according to claim 1, wherein the metadata input 2 comprises a user interface element 8 for enabling a user to enter one or more information fields relating to any or each of the subjects.

The metadata input 2 may be arranged for receiving metadata 15 indicative of an identifier of an individual one of the subjects. This identifier 15 may be associated with the separate volume image dataset 7 by the metadata handler 5, in the way described above. Furthermore, the metadata handler 5, may be arranged for associating an identifier of the input volume image dataset with the separate volume image dataset.

The system may further comprise a subsystem for performing data mining of, among others, the separate volume image datasets generated by the system from one or more input volume image datasets. Such a data mining subsystem may comprise a query input 9 for receiving a query. For example, the query input 9 is arranged for receiving a query from a user. Alternatively, a predefined query may be retrieved from another source. A search engine 10 may be arranged for searching the separate volume image datasets 16 as input for one or more separate volume image dataset 7 as output 11 for which the metadata matches the query.

The system may be implemented as a computer workstation, for example a pre-clinical workstation.

An image scanner 14 may be operatively coupled to the volume input 1 to provide the input volume image dataset. The image scanner 14 may be arranged for generating MR, PET, SPECT, ultrasound, or CT images. Other imaging modalities may also be used. The image scanner 14 may comprise a medical image scanner suitable for scanning humans. The image scanner 14 may allow sufficient space for a plurality of subjects, such as small animals, to be scanned at once, resulting in an input volume image dataset comprising a representation of a plurality of subjects. The system for processing multi-subject volumes may comprise the image scanner 14 to form an image acquisition apparatus.

Figure 2:
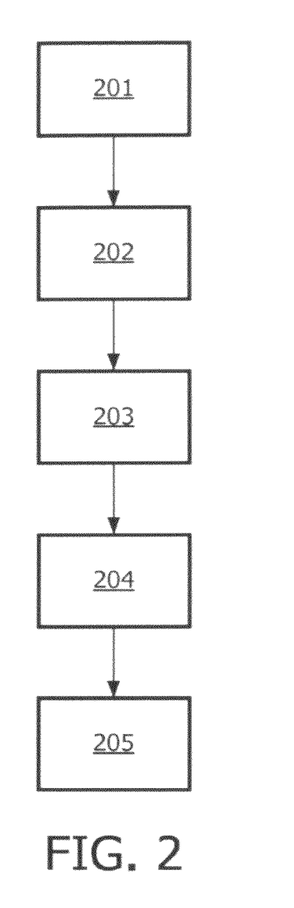
FIG. 2 is a diagram of a method of processing multi-subject volumes.

FIG. 2 illustrates a method of processing multi-subject volumes. The method comprises a step 201 of receiving an input volume image dataset comprising a plurality of subjects scanned simultaneously. The input volume image dataset may be received from a memory or from an image scanner, for example. In step 202, metadata relating to individual ones of the subjects is received. The method may comprise enabling a user to input the metadata. Alternatively, the method may comprise retrieving the metadata from a memory or from another source, for example from the image scanner. The method further may comprise step 203 of identifying a plurality of portions of the input volume image dataset, each portion comprising one of the subjects. This step may be performed independently of the step of receiving the metadata. Alternatively, the metadata is indicative of the number of subjects in the input volume image dataset, and this information is used to identify a corresponding number of portions. Other information in the metadata may be used in the identifying step 203, for example information about the shape of the subject or the position of the subject in the input volume image dataset. The method may further comprise step 204 of generating a plurality of separate volume image datasets, each separate volume image dataset comprising one of the portions of the input volume image dataset. Consequently, each separate volume image dataset comprises one of the subjects. The method may further comprise step 205 of associating the metadata relating to a subject with the separate volume image dataset comprising the portion comprising the subject. To this end, the metadata may comprise information about the relative and/or absolute positions of the subject in the input volume image dataset. Such information may be used to associate the correct metadata with the correct separate volume image dataset.

The method may be implemented as a computer program product.

The techniques described herein may, among other things, allow easy access and/or data management of image scans and quantitative results pertaining to group studies. The presence of multiple subjects in an imaging scan may pose a challenge in preclinical research workflow. In the presence of multiple subjects, associating relevant subject ID, group name and analysis data with the subject may become cumbersome. The archived separate volume image datasets can be retrieved based on group attributes such as strain name, group name, in particular if those attributes are included in the metadata. The image analysis user interface of existing preclinical applications can be customized for associating analyzed data or statistical results with a given subject's imaging data. This can lead to better integration of quantification data with the imaging study.

The user interface may enable collecting a set of information about a discovery project such as: principal investigator, groups involved in the study, and subjects associated with each group. The discovery projects may be accessed and stored by project name, allowing subject data associated with a given project to be stored together.

Figure 3:
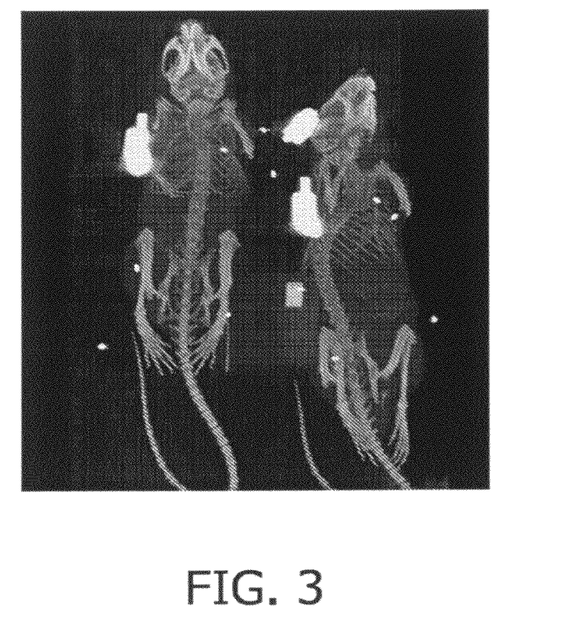
FIG. 3 is a visualization of an image dataset comprising two subjects.

A hierarchy of data in a preclinical group study may comprise different projects performed at an institution. A project may comprise a number of groups of subjects. Each group may be exposed to a different kind of experiment. Each group may comprise a plurality of subjects. For high-throughput use of imaging equipment, a number of subjects may be scanned simultaneously. For example, FIG. 3 shows a visualization of an input volume image dataset comprising two subjects. These subjects do not necessarily belong to the same group and/or project. This may make the data cumbersome to use, because the input volume image dataset does not belong to a single group and/or project.

The presence of multiple subjects and subjects from different study groups in an imaging scan poses a challenge in workflow. In the presence of subjects from a study group in an imaging study, associating relevant subject ID, group name and analysis data with the subject becomes cumbersome. For example, an image format such as DICOM can store information pertaining to a single subject. The techniques described herein facilitate generating volumetric data per subject from an imaging scan containing volumetric data of multiple subjects and storing volumetric data of a subject as a separate DICOM series. The method may automatically determine presence of multiple subjects in a given scan and generate new volumetric data per subject. The generated volumetric data per subject can be saved as a new DICOM series for better workflow management and integration of the generated analysis data (in the later part of the workflow) with the subject.

Metadata attributes associated with a subject may comprise, for example, project ID, project name, project description, principal investigator, study, study ID, study description, technologist, modality type, scan type, acquisition protocol, reconstruction protocol, strain name, and/or study type (individual or group).

Returning to FIG. 1, the subject finder 3 may be implemented in many different ways. A segmentation algorithm may be used to segment the subjects and determine a bounding box around a subject, for example.

Figure 4:
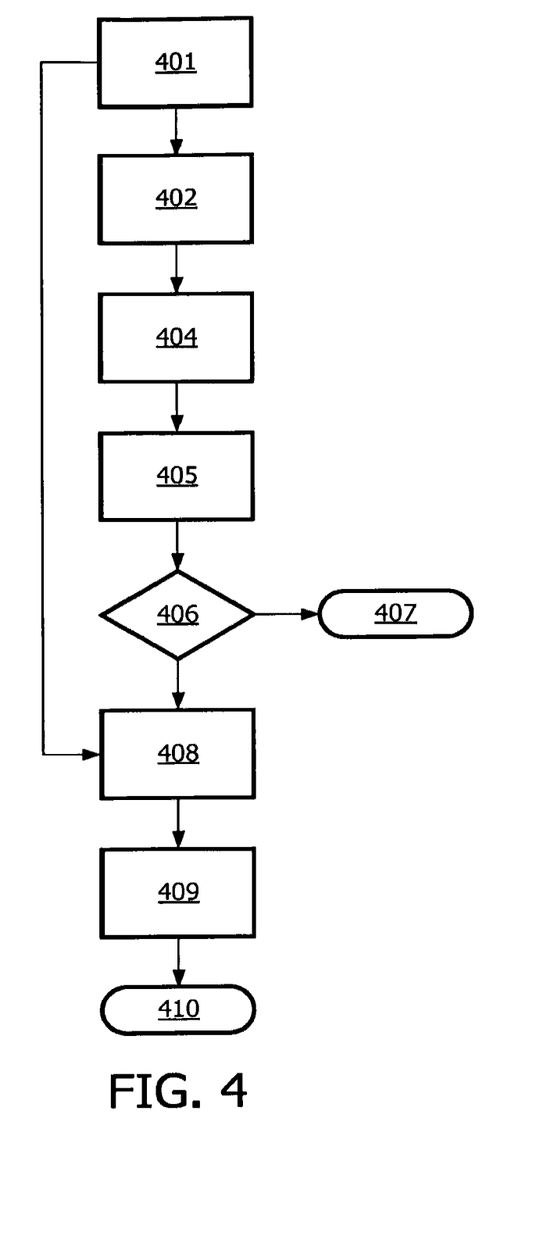
FIG. 4 is a diagram of an example process for finding multiple subjects in a volume.
Figure 5:
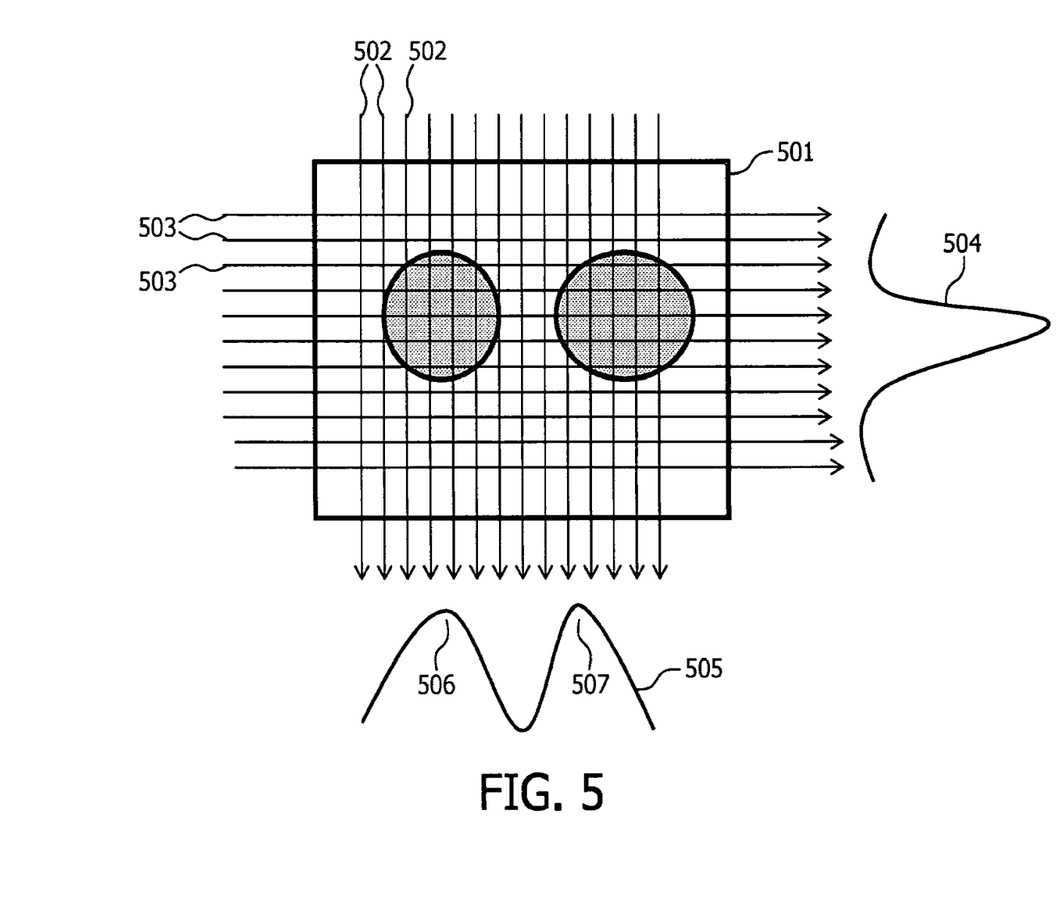
FIG. 5 shows a sketch of a mid-slice of an input volume image dataset.
Figure 6:
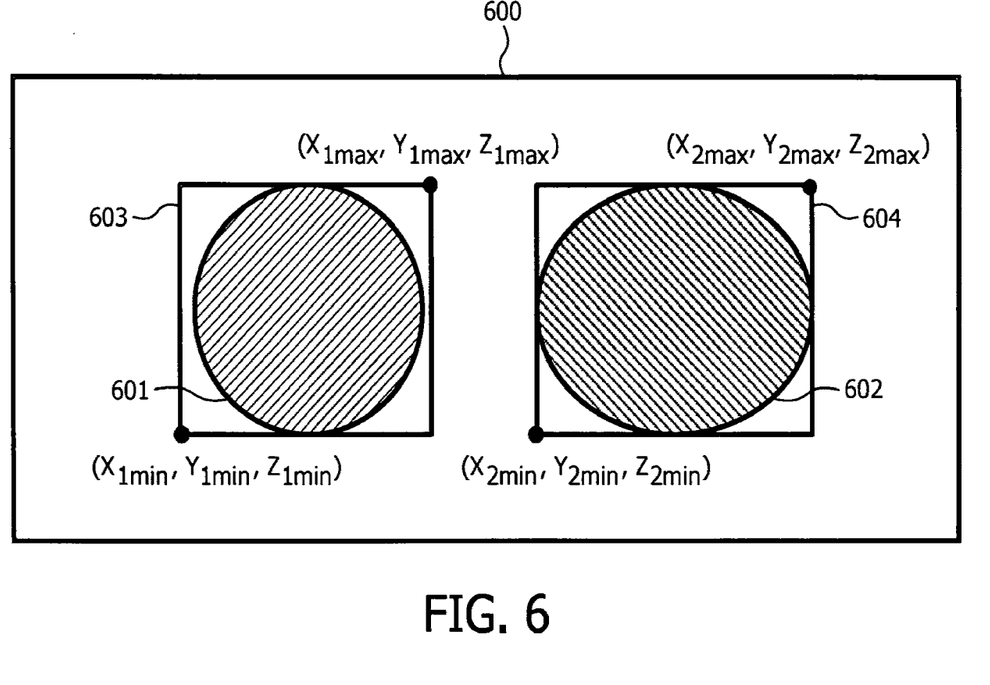
FIG. 6 shows a two-dimensional sketch of a three-dimensional image volume dataset.

FIG. 4 shows an example process which may be performed by the subject finder 3. This process will be explained with reference to examples shown in FIG. 5, which illustrates a mid-slice of the input volume image dataset, and FIG. 6 which illustrates an example two-dimensional sketch of a three-dimensional image volume dataset. First, in step 401 an input volume image dataset is received. If it is already known that it comprises more than one subject, the flow proceeds at step 408. Otherwise, first it is checked whether more than one subject is present in the input volume image dataset. For example, steps 402-406 may be used as follows. In step 402, a mid-slice 501 may be extracted from a volumetric dataset acquired from medical imaging modalities. In step 404, ray sum technique may be used to create probability distribution functions along two axes of the mid-slice. For every column 502 or row 503 of image elements in the mid-slice 501, a ray sum may be computed by counting the number of pixels with intensity values greater than a threshold. Other ways of computing a ray sum are also possible. In step 405, the presence of multiple subjects in the imaging study may be detected by the presence of multiple peaks in either one or both of the estimated probability distributions (i.e. row probability distribution 504 or column probability distribution 505). In the example of FIG. 5, the two peaks 506 and 507 in the column probability distribution 505 indicate that there are two subjects in the image dataset. In step 406, the process ends at terminator 407 if multiple subjects were not detected, otherwise the process continues by identifying a plurality of portions of the input volume image dataset, each portion comprising one of the subjects. For example, this may be done with steps 408-409 as described in the following. In step 408, automatic segmentation and labeling of a subject's volumetric data may be performed. A threshold and 3D connected component labeling algorithm may be used to segment and label subjects in the volumetric dataset. The connected component labeling scans the volumetric dataset and groups its voxels into components based on voxel connectivity (the voxels having similar intensity characteristics). At the end of the connected component labeling, each subject's volumetric data may be given a distinct label. In step 409, a volume of interest may be defined for each subject. For example, the bounding box, (by means of corner coordinates (Xmin, Ymin, Zmin) and (Xmax, Ymax, Zmax)) may be computed for each label. FIG. 6 illustrates an example two-dimensional sketch of a three-dimensional image volume dataset 600 with two bounding boxes 603 and 604 for respective subjects 601 and 602. The computed bounding box represents the volume of interest of the subject or sub-volume containing the volumetric data of the subject. In step 410, the three-dimensional image volume dataset 600 and bounding boxes 603 and 604 are forwarded to the volume image dataset generator 4, which may save each sub-volume per subject as a separate volume image dataset 7, for example formatted as a new DICOM series.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for processing multi-subject volumes, comprising:
 a volume input configured to receive an input volume image dataset comprising multiple patients scanned simultaneously;
 a metadata input configured to receive metadata relating to individual ones of the multiple subjects;
 a subject finder configured to identify a plurality of portions of the input volume image dataset, each portion comprising one of the multiple patients;
 a volume image dataset generator configured to generate a plurality of separate volume image datasets, each separate volume image dataset comprising one of the portions of the input volume image dataset; and
 a metadata handler configured to associate the metadata relating to one of the multiple patients with the separate volume image dataset comprising the portion comprising the subject.

2. The system according to claim 1, wherein the volume image dataset generator comprises a file generator configured to generate files, each file including one of the separate volume image datasets, and the metadata handler is operatively connected to the volume image dataset generator and configured to include the metadata of the patient corresponding to the one of the separate volume image datasets.

3. The system according to claim 1, wherein each separate volume image dataset is in a DICOM format and wherein the metadata are represented as DICOM attributes.

4. The system according to claim 1, wherein the volume input is configured to receive the input volume image dataset in a DICOM format and the volume image data set generator is configured to generate the plurality of volume image datasets, each in the DICOM format.

5. The system according to claim 1, wherein the multiple patients include laboratory animals that belong to different study groups, and the metadata is indicative of the study group each patient belongs to.

6. The system according to claim 1, wherein the metadata input comprises a user interface element configured to enable a user to enter information fields relating to each of the multiple patients.

7. The system according to claim 1, wherein the metadata input is configured to receive metadata indicative of each identifier of an individual one of the multiple patients.

8. The system according to claim 1, wherein the metadata handler is arranged for associating an identifier of the input volume image dataset with the separate volume image dataset.

9. The system according to claim 1, further comprising:
a query input configured to receive a query;
a search engine configured to search the plurality of separate volume image datasets for one or more of the separate volume image datasets with the metadata matching the query.

10. An image acquisition apparatus comprising an image scanner for acquiring an input volume image dataset comprising multiple patients scanned simultaneously, and the system according to claim 1.

11. A pre-clinical workstation comprising the system according to claim 1.

12. A method of processing multi-subject volumes, comprising:
receiving an input volume image dataset comprising multiple patients scanned simultaneously;
receiving metadata relating to individual ones of the multiple patients;
identifying a plurality of portions of the input volume image dataset, each portion comprising one of the multiple patients;
generating a plurality of separate volume image datasets, each separate volume image dataset comprising one of the portions of the input volume image dataset; and
associating the metadata relating to one of the multiple patients with the separate volume image dataset comprising the portion comprising the subject.

13. A non-transitory computer program product comprising instructions for causing a processor system to perform the method according to claim 12.

14. The method according to claim 12, wherein identifying each portion includes coordinates of a bounding box around each of the multiple patients, wherein the patients include laboratory animals.

15. The method according to claim 12, wherein identifying the plurality of portions includes determining presence of each of the multiple patients in the input volume image dataset by ray sums along two axes of a mid-slice of the input volume image dataset.

16. The method according to claim 12, wherein the input volume image dataset is in DICOM format including metadata which identifies the input volume image dataset represented as DICOM attributes and each separate volume image dataset is in DICOM format with metadata which identifies the separate volume image dataset and the metadata identifies the volume image dataset represented as DICOM attributes.

17. A system for processing volume images of multiple laboratory animals, comprising:
one or more processors programmed to:
receive a volume image dataset including image data of multiple individual laboratory animals scanned simultaneously;
identify portions of the received volume image dataset corresponding to each of the individual multiple laboratory animals;
receive metadata corresponding to each of the individual multiple laboratory animals;
generate a plurality of separate volume image datasets, each separate volume image dataset corresponding to one of the individual laboratory animals and associated with the received metadata corresponding to the same individual subject laboratory animal; and
one or more databases configured to receive and store the associated separate volume image datasets with the associated metadata in a searchable format.

18. The system according to claim 17, wherein the multiple laboratory animals are involved in different studies and wherein the received metadata includes a study group and an identifier of the input volume image dataset.

19. The system according to claim 17, further including:
a search engine configured to receive a query input and search the one or more databases for one or more separate volume image datasets with associated metadata that matches the query input.

* * * * *